United States Patent
Voelker et al.

(10) Patent No.: US 9,579,301 B2
(45) Date of Patent: Feb. 28, 2017

(54) ORGANIC EMULSION COMPRISING DHA AND EPA

(71) Applicant: DSM IP ASSETS B.V., Heerlen (NL)

(72) Inventors: Karl Manfred Voelker, Basel (CH); Denis Hug, Basel (CH); Thomas Lindemann, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 315 days.

(21) Appl. No.: 14/371,840

(22) PCT Filed: Jan. 11, 2013

(86) PCT No.: PCT/EP2013/050447
§ 371 (c)(1),
(2) Date: Jul. 11, 2014

(87) PCT Pub. No.: WO2013/104740
PCT Pub. Date: Jul. 18, 2013

(65) Prior Publication Data
US 2014/0356464 A1 Dec. 4, 2014

(30) Foreign Application Priority Data
Jan. 11, 2012 (EP) .................................... 12150757

(51) Int. Cl.
| | | |
|---|---|---|
| *A01N 65/00* | (2009.01) | |
| *A61K 31/202* | (2006.01) | |
| *A61Q 19/00* | (2006.01) | |
| *A61K 9/107* | (2006.01) | |
| *A23D 7/005* | (2006.01) | |
| *A23D 7/01* | (2006.01) | |
| *A61K 36/53* | (2006.01) | |
| *A61K 8/36* | (2006.01) | |
| *A61K 8/362* | (2006.01) | |
| *A61K 8/65* | (2006.01) | |
| *A61K 8/67* | (2006.01) | |
| *A61K 8/97* | (2006.01) | |
| *A61K 8/06* | (2006.01) | |
| *A23D 7/06* | (2006.01) | |
| *A61K 31/341* | (2006.01) | |
| *A61K 31/355* | (2006.01) | |

(52) U.S. Cl.
CPC .......... *A61K 31/202* (2013.01); *A23D 7/0053* (2013.01); *A23D 7/011* (2013.01); *A23D 7/06* (2013.01); *A23K 20/158* (2016.05); *A23L 33/105* (2016.08); *A23L 33/115* (2016.08); *A23L 35/10* (2016.08); *A61K 8/06* (2013.01); *A61K 8/361* (2013.01); *A61K 8/362* (2013.01); *A61K 8/65* (2013.01); *A61K 8/676* (2013.01); *A61K 8/678* (2013.01); *A61K 8/97* (2013.01); *A61K 9/107* (2013.01); *A61K 31/341* (2013.01); *A61K 31/355* (2013.01); *A61K 36/53* (2013.01); *A61Q 19/00* (2013.01); *A23V 2002/00* (2013.01); *A61K 2800/10* (2013.01)

(58) Field of Classification Search
CPC ...................................................... A61K 36/00
USPC ........................................................ 424/725
See application file for complete search history.

(56) References Cited

U.S. PATENT DOCUMENTS

2010/0055281 A1    3/2010  Barrow et al.

FOREIGN PATENT DOCUMENTS

| | | |
|---|---|---|
| CN | 101472485 | 7/2009 |
| JP | 2009-533490 | 9/2009 |
| WO | WO 2007/120500 | 10/2007 |
| WO | WO 2011/127163 | 10/2011 |

OTHER PUBLICATIONS

International Search Report for PCT/EP2013/050447, mailed Mar. 3. 2013.
EP Search Report for EP Application No. 12150757, dated Apr. 27, 2012.
Surh, J. et al., "Properties and stability of oil-in-water emulsions stabilized by fish gelatin", Food Hydrocolloids, vol. 20, No. 5, (Jul. 1, 2996), pp. 596-606.
Frankel, E.N. et al., "Evaluation of Antioxidant Activity of Rosemary Extracts, Carnosol and Carnosic Acid in Bulk Vegetable Oils and Fish Oil and their Emulsions", Journal of the Science of Food and Agriculture, vol. 72, No. 2, (Oct. 1, 1996), pp. 201-208.
Wada et al, "The Synergistic Antioxidant Effect of Rosemary Extract and α-Tocopherol in Sardine Oil Model System and Frozen-Crushed Fish Meat", *Journal of Food Processing and Preservation* 16(1992) 263-274.

*Primary Examiner* — Michael Meller
(74) *Attorney, Agent, or Firm* — Nixon & Vanderhye P.C.

(57) ABSTRACT

The present invention relates to an emulsion of an oil composition comprising docasoahexaenoic acid (DHA) and eicosapentaenoic acid (EPA), which is characterized in that the emulsion is essentially free from ascorbyl palmitate.

6 Claims, No Drawings

ORGANIC EMULSION COMPRISING DHA AND EPA

This application is the U.S. national phase of International Application No. PCT/EP2013/050447, filed 11 Jan. 2013, which designated the U.S. and claims priority to EP Application No. 12150757.8, filed 11 Jan. 2012, the entire contents of each of which are incorporated herein by reference.

The present invention relates to an emulsion of an oil composition comprising docasoahexaenoic acid (DHA) and eicosapentaenoic acid (EPA), which is characterised in that the emulsion is essentially free from ascorbyl palmitate.

Emulsions of PUFA oils are well known. They can be used in many fields of applications and they are used in liquid or in dry form.

PUFA oils, which are polyunsaturated fatty acids, are very prone to oxidise. Due to that fact, emulsions usually comprise ingredients to prevent the oxidation of the oils.

On the other hand there is a strong tendency to provide emulsions, which are natural and/or organic.

The terms "natural" and "organic" in the context of the present invention are related to the legal definitions set by the country they are sold in:

For example in the European Union there is the EU-Eco-regulation, in the United States there are the National Organic Program (NOP) Standards and Japan there are the JAS Standards.

The goal of the present invention was to provide an emulsion comprising docasoahexaenoic acid (DHA) and eicosapentaenoic acid (EPA) oils and which is natural and/or organic according to the national regulations (especially the ones in Europe (EU), USA, Japan and China).

Therefore the present invention relates to an emulsion comprising
5-40 weight-% (wt-%), based on the total weight of the emulsion, of docasoahexaenoic acid (DHA) and eicosapentaenoic acid (EPA) oils, and
3-15 wt-%, based on the total weight of the emulsion, of at least one emulsifier, and
1-5 wt-%, based on the total weight of the emulsion, of ascorbic acid and/or citric acid,
0.5-5 wt-%, based on the total weight of the emulsion, of at least one base, and
35-90.5 wt-%, based on the total weight of the emulsion, of water, and
150 ppm-1000 ppm of at least one tocopherol, and
1000 ppm-5000 ppm of rosemary extract,
whereby
the pH value of the emulsion is between 5 and 7, and
the emulsion is essentially free of ascorbyl palmitate, and
the emulsion is natural and/or organic.

In the context of the present invention essentially free of ascorbyl palmitate (AP) means, that the emulsion according to the present invention still is regarded as "organic" and/or "natural" according to the legal definition of "organic" and "natural".

All ingredients of the emulsion according to the present invention are natural and/or organic. This means that all ingredients of the emulsion are produced (or extracts) by using a natural and/or an organic process.

The DHA and EPA oils can be from any natural and/or organic source, such as plants and/or animals. One source of omega-3 fatty acids, such as DHA, includes an animal source. Examples of animal sources include aquatic animals (e.g., fish, marine mammals, and crustaceans such as krill and other euphausids) and animal tissues (e.g., brain, liver, eyes, etc.) and animal products such as eggs or milk. DHA and EPA can be purified to various levels. Such a purification can be achieved by any means known to those of skill in the art. In the context of the present invention the purification must allow that the purified oil is natural and/or organic.

Additional fatty acids can be present in the oil. These fatty acids can include fatty acids that were not removed during the purification process, i.e., fatty acids that were co-isolated with DHA and EPA from the source. These fatty acids can be present in various concentrations. In some embodiments, the oil comprises 0.1% to 60% of one or more of the following fatty acids, or esters thereof: (a) capric acid; (b) lauric acid; (c) myristic acid; (d) palmitic acid, (e) palmitoleic acid; (f) stearic acid; (g) oleic acid; (h) linoleic acid; (i) α-linolenic acid; (j) docosapentaenoic acid 22:5n-3, 22:5w3 (DPAn3); and (k) 4,7,10,13,16,19,22,25 octacosaoctaenoic acid (C28:8). All of these oils also fulfill the criteria of natural and/or organic.

The emulsifiers used in the emulsions according to the present invention are also natural and/or organic. Such emulsifier can be from any source. suitable emulsifiers for emulsion according to the present invention are lecithin, whey proteins, gum acacia (water extracted), hydrolysed collagene, pectin and fish gelatine. Especially preferred is fish gelatine.

The ascorbic acid as well as the citric acid is natural and/or organic. Usually they are sourced from a plant.

The base used in the emulsion according to the present invention can be (chemically) organic or inorganic. But the base must always fulfil the criteria of the legal term organic as described above. An especially preferred base is NaOH.

By the term "tocopherol", there is meant d1-α-tocopherol, d-□-tocopherol, □, and □-tocopherol and mixtures thereof, whereby the tocopherols used in the emulsion according to the present invention are natural and/or organic.

In some embodiments the tocopherol is present in the emulsion in an amount of from 150 ppm to 1000 ppm, in preferred embodiments the tocopherol is present from 200 to 800 ppm.

The tocopherol (or a mixture of tocopherols) can be mixed to the emulsion or it can be mixed into the PUFA oil first and then added as mixture to the emulsion.

The emulsion according to the present invention comprises rosemary extract.

By the expression "rosemary extract" there is meant any extracts obtainable from rosemary which have antioxidant activity. The extraction is carried out in such a way that the obtained rosemary extract is natural and/or organic.

Rosemary (*Rosmarinus officinalis*, Labiatae) is a ubiquitous plant in the Mediterranean area and is characterised by antioxidant and antimicrobial pharmacological properties.

Rosemary extract is a natural and known material extracted from the rosemary plant.

The rosemary extract may be obtained by drying leaves of rosemary, which belongs to the Perilla family, pulverizing the dried leaves, and subjecting the resultant pulverized material to extraction with water, hot water, hexane, ethanol, acetone, ethyl acetate, or a mixture of any of these solvents. The term "rosemary extract" as used herein is a generic term describing a number of different chemical compositions that may contain several different active components. Among the common components that are found in rosemary extract are: caffeic acid; carnosol; carnosic acid; methoxy carnosic acid; rosmarinic acid; rosmanol; and rosmaridiphenol; all of which may be present in different proportions depending on the individual extract. Numerous rosemary extracts are also available commercially, and any one or more can be used in the present invention.

Suitable rosemary extracts are i.e. commercially available from companies such as Kalsec (Kalamazoo, Mich., USA) or Naturex (Avignon, France).

The emulsions according to the present invention comprise 1000 ppm-5000 ppm of the rosemary extract, preferred 500 ppm to 4000 ppm, more preferred 500 to 3500 ppm.

Furthermore, the present invention relates to a process for producing an emulsion according to the present invention wherein all ingredients as well as all process steps are natural and/or organic.

The emulsions according to the present invention can be used in any applications, wherein such emulsions are needed.

The emulsions can be used i.e. in food, feed or personal care products.

These products can be in any form, such as liquid, gel-like or solid. These products can be ready to use (ready to consume) products as well as products which need to be further processed (for example by dilution, dissolving, heating, etc)

Especially important is the use of such emulsions is in food products, such as beverages.

The following examples illustrate the invention. The sensory values and the rancimat values are determined as described above.

EXAMPLE

| Ingredients | Amount [Wt-%] |
|---|---|
| EPA | 4.8 |
| DHA | 3 |
| Fish gelatine | 8.0 |
| Ascorbic acid | 2.2 |
| NaOH (50% aq solution) | 1.0 |
| Water content (total) | 62.8 |
| Other oils | 18.2 |

The emulsion produced by preparing the oil phase and the water phase separately and then homogenizing the oil phase into the water phase by means of an appropriate pre-homogenizing device (such as a rotor-stator, micer disk, etc) and subsequently applying a high pressure homogenization. pH-value of this emulsion is 6.

This natural and organic emulsion is storage stable and easy to incorporate into any formulation.

The invention claimed is:

1. An emulsion consisting essentially of:
   (i) 5-40 wt-%, based on the total weight of the emulsion, of docasoahexaenoic acid (DHA) and eicosapentaenoic acid (EPA) oils,
   (ii) 3-15 wt-%, based on the total weight of the emulsion, of fish gelatin,
   (iii) 1-5 wt-%, based on the total weight of the emulsion, of ascorbic acid and/or citric acid,
   (iv) 0.5-5 wt-%, based on the total weight of the emulsion, of NaOH,
   (v) 35-90.5 wt-%, based on the total weight of the emulsion, of water,
   (vii) 150 ppm-1000 ppm of at least one tocopherol, and
   (vii) 1000 ppm-5000 ppm of rosemary extract, wherein the emulsion is essentially free of ascorbyl palmitate and the pH of the emulsion is between 5 and 7.

2. The emulsion of claim 1, wherein the emulsion is natural and/or organic.

3. The emulsion of claim 1, wherein the tocopherol is selected from the group consisting of dl-a-tocopherol, d-a-tocopherol, β-tocopherol, γ-tocopherol, and δ-tocopherol.

4. The emulsion of claim 1, wherein the at least one tocopherol is present in an amount of 200 to 800 ppm.

5. The emulsion of claim 1, wherein the rosemary extract is present in an amount of 500 to 4000 ppm.

6. A food, a feed or a personal care product consisting essentially of the emulsion of claim 1.

* * * * *